United States Patent
Zhao et al.

(10) Patent No.: US 10,736,621 B2
(45) Date of Patent: Aug. 11, 2020

(54) SYSTEM AND METHOD FOR MONITORING OF A MECHANICAL FORCE

(71) Applicants: MAYO FOUNDATION FOR MEDICAL EDUCATION AND RESEARCH, Rochester, MN (US); MICHIGAN TECHNOLOGICAL UNIVERSITY, Houghton, MI (US)

(72) Inventors: Chunfeng Zhao, Rochester, MN (US); Kai-Nan An, Rochester, MN (US); Keat Ghee Ong, Houghton, MI (US); Andrew DeRouin, Houghton, MI (US)

(73) Assignees: Mayo Foundation for Medical Education and Research, Rochester, MN (US); Michigan Technology University, Houghton, MI (US)

( * ) Notice: Subject to any disclaimer, the term of this patent is extended or adjusted under 35 U.S.C. 154(b) by 195 days.

(21) Appl. No.: 15/553,011

(22) PCT Filed: Feb. 25, 2016

(86) PCT No.: PCT/US2016/019552
§ 371 (c)(1),
(2) Date: Aug. 23, 2017

(87) PCT Pub. No.: WO2016/140861
PCT Pub. Date: Sep. 9, 2016

(65) Prior Publication Data
US 2018/0049733 A1   Feb. 22, 2018

Related U.S. Application Data

(60) Provisional application No. 62/121,623, filed on Feb. 27, 2015.

(51) Int. Cl.
*A61B 17/04* (2006.01)
*A61B 17/06* (2006.01)
(Continued)

(52) U.S. Cl.
CPC .... *A61B 17/0401* (2013.01); *A61B 17/06166* (2013.01); *G01L 1/125* (2013.01);
(Continued)

(58) Field of Classification Search
CPC .......... A61B 17/0401; A61B 17/06166; A61B 2090/064; A61B 2017/044;
(Continued)

(56) References Cited

U.S. PATENT DOCUMENTS

| | | | | |
|---|---|---|---|---|
| 4,896,544 A * | 1/1990 | Garshelis | ................ | G01L 3/102 73/862.333 |
| 5,052,232 A * | 10/1991 | Garshelis | ................ | G01L 3/102 73/862.336 |

(Continued)

FOREIGN PATENT DOCUMENTS

JP        05281063 A  * 10/1993

OTHER PUBLICATIONS

Gill et al. "Device for measuring the force required to close a surgical wound". Med & Biol. Eng. & Comput. 1987, 25, 219-221. <https://link.springer.com/content/pdf/10.1007/BF02442854.pdf> (Year: 1987).*

(Continued)

*Primary Examiner* — Jonathan M Dunlap
(74) *Attorney, Agent, or Firm* — Quarles & Brady LLP

(57) ABSTRACT

Systems and methods for monitoring a mechanical force applied to a wound site repairing structure are disclosed. In an embodiment, the systems include a wound site repairing structure, a magnetoelastic sensor coupled to the wound site repairing structure, and a detection system. The detection system includes an excitation coil configured to transmit a signal to the magnetoelastic sensor and a detection coil configured to detect a signal indicative of a mechanical force applied to the wound site repairing structure. The detection (Continued)

system also includes a detection unit configured to detect the signal indicative of the mechanical force applied to the wound repairing structure.

23 Claims, 14 Drawing Sheets

(51) Int. Cl.

| | |
|---|---|
| G01L 1/12 | (2006.01) |
| G01L 5/102 | (2020.01) |
| G01L 5/103 | (2020.01) |
| A61B 17/00 | (2006.01) |
| A61B 90/00 | (2016.01) |
| A61N 2/00 | (2006.01) |
| A61N 2/06 | (2006.01) |
| A61N 2/02 | (2006.01) |
| A61N 1/32 | (2006.01) |
| A61B 17/80 | (2006.01) |
| A61N 7/00 | (2006.01) |
| G01B 7/16 | (2006.01) |
| A61N 1/05 | (2006.01) |

(52) U.S. Cl.
CPC .............. *G01L 5/102* (2013.01); *G01L 5/103* (2013.01); *A61B 17/8014* (2013.01); *A61B 17/8023* (2013.01); *A61B 2017/00004* (2013.01); *A61B 2017/00039* (2013.01); *A61B 2017/00115* (2013.01); *A61B 2017/00221* (2013.01); *A61B 2017/00876* (2013.01); *A61B 2017/044* (2013.01); *A61B 2017/0412* (2013.01); *A61B 2017/0414* (2013.01); *A61B 2090/064* (2016.02); *A61N 1/05* (2013.01); *A61N 1/326* (2013.01); *A61N 2/002* (2013.01); *A61N 2/004* (2013.01); *A61N 2/02* (2013.01); *A61N 2/06* (2013.01); *A61N 7/00* (2013.01); *A61N 2007/0013* (2013.01); *G01B 7/16* (2013.01)

(58) Field of Classification Search
CPC .... A61B 2017/0414; A61B 2017/0412; A61B 2017/00876; A61B 2017/00221; A61B 2017/00039; A61B 2017/00004; A61B 2017/00115; A61B 17/8023; A61B 17/8014; G01L 1/125; G01L 5/103; G01L 5/102; A61N 2/002; A61N 2/06; A61N 2/02; A61N 2/004; A61N 1/326; A61N 2007/0013; A61N 1/05; A61N 7/00; G01B 7/16

See application file for complete search history.

(56) References Cited

U.S. PATENT DOCUMENTS

| | | | | |
|---|---|---|---|---|
| 5,437,197 | A | 8/1995 | Uras et al. | |
| 5,646,356 | A | 7/1997 | Ling et al. | |
| 6,397,661 | B1* | 6/2002 | Grimes | G01K 7/38 |
| | | | | 324/207.13 |
| 6,521,140 | B2* | 2/2003 | Yoshida | H01F 1/28 |
| | | | | 252/62.54 |
| 7,113,876 | B2* | 9/2006 | Zeng | G01N 29/032 |
| | | | | 324/236 |
| 7,813,857 | B2* | 10/2010 | Mizon | B60K 23/0808 |
| | | | | 192/54.1 |
| 7,913,569 | B2* | 3/2011 | Girshovich | G01B 7/16 |
| | | | | 324/209 |
| 9,645,022 | B2* | 5/2017 | Brummel | G01L 3/105 |
| 9,726,557 | B2* | 8/2017 | Gianchandani | H01L 41/125 |
| 2002/0166382 | A1 | 11/2002 | Bachas et al. | |
| 2004/0113801 | A1* | 6/2004 | Gustafson | A61F 13/2051 |
| | | | | 340/604 |
| 2006/0016277 | A1* | 1/2006 | Nehl | G01L 3/102 |
| | | | | 73/862.333 |
| 2007/0222767 | A1* | 9/2007 | Wang | G01C 21/3664 |
| | | | | 345/173 |
| 2008/0015582 | A1 | 1/2008 | DiPoto et al. | |
| 2008/0027484 | A1 | 1/2008 | Lee et al. | |
| 2008/0173102 | A1 | 7/2008 | Nehl et al. | |
| 2009/0076597 | A1* | 3/2009 | Dahlgren | A61B 17/7016 |
| | | | | 623/2.1 |
| 2009/0082934 | A1* | 3/2009 | Mizon | B60K 23/0808 |
| | | | | 701/68 |
| 2009/0131838 | A1* | 5/2009 | Fotiadis | A61B 5/0031 |
| | | | | 601/2 |
| 2009/0302498 | A1* | 12/2009 | Nedestam | A61F 13/42 |
| | | | | 264/263 |
| 2012/0083806 | A1* | 4/2012 | Goertzen | A61B 17/0401 |
| | | | | 606/151 |
| 2013/0150685 | A1 | 6/2013 | Toth | |
| 2013/0218048 | A1* | 8/2013 | Hayden | G01R 33/18 |
| | | | | 600/577 |
| 2014/0228880 | A1 | 8/2014 | Bisson et al. | |
| 2014/0366637 | A1* | 12/2014 | Brummel | G01L 3/105 |
| | | | | 73/779 |
| 2015/0122044 | A1* | 5/2015 | Gianchandani | H01L 41/125 |
| | | | | 73/779 |

OTHER PUBLICATIONS

Kitagawa et al. "Effect of sensory substitution on suture-manipulation forces for robotic surgical systems". The Journal of Thoracic and Cardiovascular Surgery, Jan. 2005, vol. 129, No. 1, 151-156 <https://www.sciencedirect.com/science/article/pii/S0022522304008876> (Year: 2005).*

Aqeel et al. "Sensory System device for Suture-Manipulation Tension Measurement for Surgery". 2012 IEEE International Conference on Electro/Information Technology, May 6-8, 2012 <https://ieeexplore.ieee.org/stamp/stamp.jsp?arnumber=6220717> (Year: 2012).*

DeRouin et al. "A Wireless Sensor for Real-Time Monitoring of Tensile Force on Sutured Wound Sites", IEEE Transactions on Biomedical Engineering, vol. 63, No. 8, Aug. 2016, <https://ieeexplore.ieee.org/stamp/stamp.jsp?tp=&arnumber=7234878> (Year: 2016).*

Oess et al. "Magnetoelastic Strain Sensor for Optimized Assessment of Bone Fracture Fixation", IEEE Sensors Journal, vol. 9, No. 8, Aug. 2009, <https://ieeexplore.ieee.org/stamp/stamp.jsp?tp=&arnumber=5155915> (Year: 2009).*

Zhiyuan et al. "Fabrication of Cable Tension Sensor Based on Magnetoelastic Effect", 2009 International Conference on Electronic Computer Technology, Feb. 27, 2009, <https://ieeexplore.ieee.org/stamp/stamp.jsp?tp=&arnumber=4796046> (Year: 2009).*

Pepakayala et al. "Passive Wireless Strain Sensors Using Microfabricated Magnetoelastic Beam Elements", Journal of Microelectromechanical Systems, vol. 23, No. 6, Dec. 2014, <https://ieeexplore.ieee.org/stamp/stamp.jsp?tp=&arnumber=6805130> (Year: 2014).*

Grimes et al. "Theory, Instrumentation and Applications of Magnetoelastic Resonance Sensors: A Review", Sensors 2001, 11, 2809-2844, Mar. 2, 2011, <https://www.ncbi.nlm.nih.gov/pmc/articles/PMC3231618/pdf/sensors-11-02809.pdf> (Year: 2001).*

Grimes et al. "Wireless Magnetoelastic Resonance Sensors: A Critical Review", Sensors 2002, 2, 294-313, Jul. 23, 2002, <https://pdfs.semanticscholar.org/08b8/06cb921057bcf10e5ce253cd05ef9012bf9d.pdf> (Year: 2002).*

Barber, et al., Suture Anchor Failure Strength—An In Vivo Study, Arthroscopy, 1993, 9(6):647-652.

Belmont Jr., et al., Disease and Nonbattle Injuries Sustained by a U.S. Army Brigade Combat Team During Operation Iraqi Freedom, Military Medicine, 2010, 175:469-476.

Bynum, et al., Failure Mode of Suture Anchors as a Function of Insertion Depth, American Journal of Sports Medicine, 2005, 33(7):1030-1034.

(56) References Cited

OTHER PUBLICATIONS

Cummins, et al., Mode of Failure for Rotator Cuff Repair with Suture Anchors Identified at Revision Surgery, Journal of Shoulder and Elbow Surgery, 2003, 12:128-133.

Derwin, et al., Extracellular Matrix Scaffold Devices for Rotator Cuff Repair, Journal of Shoulder and Elbow Surgery, 2010, 19(3):467-476.

Holmes, et al., Biodegradation and Biocompatibility of Mechanically Active Magnetoelastic Materials, Smart Materials and Structures, 2014, 23:095036, 5 pages.

Horeman, et al., Force Sensing in Surgical Sutures, PLOS ONE, 2013, 8(12):e84466, 12 pages.

Kim, et al., Thin, Flexible Sensors and Actuators as 'Instrumented' Surgical Sutures for Targeted Wound Monitoring and Therapy, Small, 2012, 8(21):3263-3268.

Meyer, et al., Failure of Suture Material at Suture Anchor Eyelets, Arthroscopy, 2002, 18(9):1013-1019.

Neyton, et al., Arthroscopic Suture-Bridge Repair for Small to Medium Size Supraspinatus Tear: Healing Rate and Retear Pattern, Arthroscopy, 2013, 29(1):10-17.

Pereles, et al., A Wireless Flow Sensor Based on Magnetic Higher-Order Harmonic Fields, Smart Materials and Structures, 2009, 18:095002 (6 pp).

Ruiz-Moneo, et al., Plasma Rich in Growth Factors in Arthroscopic Rotator Cuff Repair: A Randomized, Double-Blind, Controlled Clinical Trial, Arthroscopy, 2013, 29(1):2-9.

Tan, et al., A Wireless Embedded Sensor Based on Magnetic Higher-Order Harmonic Fields: Application to Liquid Pressure Monitoring, IEEE Sensors Journal, 2010, 10(6):1085-1090.

Tan, et al., Design, Fabrication, and Implementation of a Wireless, Passive Implantable Pressure Sensor Based on Magnetic Higher-Order Harmonic Fields, Biosensors, 2011, 1:134-152.

Tan, et al., Magnetoelastic-Harmonic Stress Sensors With Tunable Sensitivity, IEEE Sensors Journal, 2012, 12 (6):1878-1883.

Van Der Meijden, et al., Rehabilitation After Arthroscopic Rotator Cuff Repair: Current Concepts Review and Evidence-Based Guidelines, International Journal of Sports Physical Therapy, 2012, 7(2):197-218.

PCT International Search Report and Written Opinion, PCT/US2016/019552, dated Jun. 2, 2016, 12 pages.

* cited by examiner

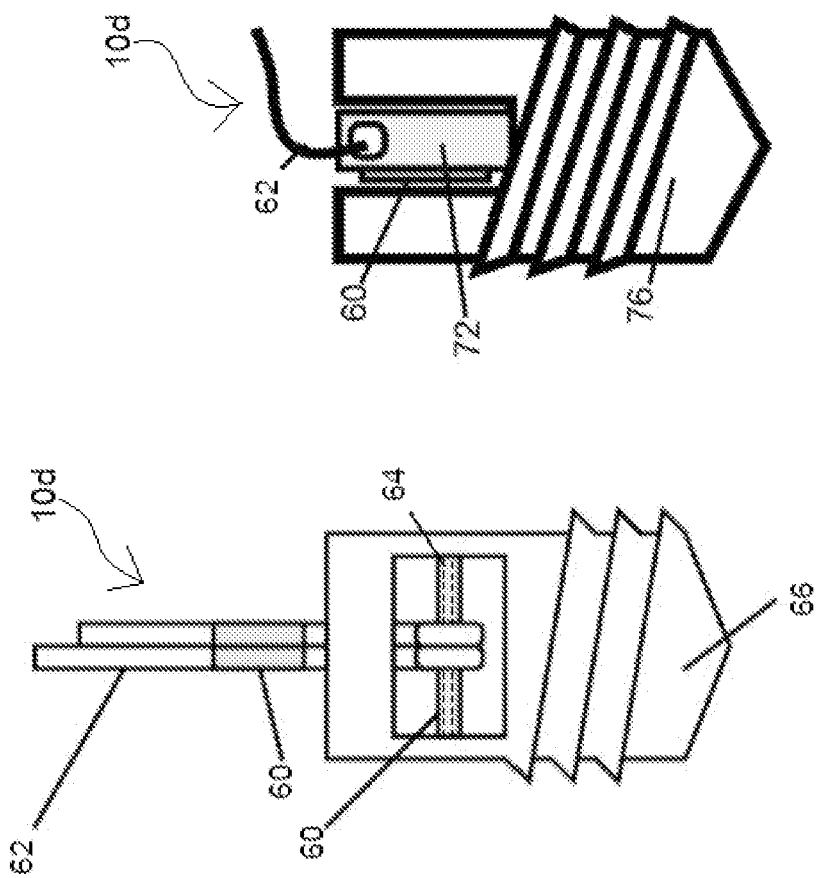
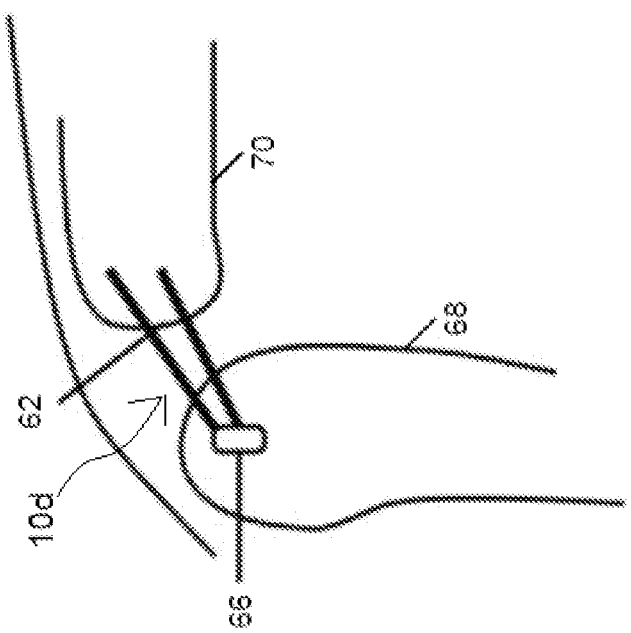
FIG. 3B
FIG. 3A
FIG. 3

SYSTEM AND METHOD FOR MONITORING OF A MECHANICAL FORCE

CROSS-REFERENCE TO RELATED APPLICATIONS

This application represents the national stage entry of PCT International Application No. PCT/US2016/019552 filed on Feb. 25, 2016 and, claims priority to, U.S. Provisional Patent Application Ser. No. 62/121,623, filed on Feb. 27, 2015, the contents of which are hereby incorporated by reference as if set forth in their entirety herein.

BACKGROUND

The present disclosure relates to systems and methods for monitoring mechanical forces. More particularly, the present disclosure relates to systems and methods for monitoring mechanical forces applied to wound site repairing structure at a wound site.

Wound site repairing structure includes surgical sutures, which are typically threads applied to a wound site using a needle to hold body tissues together. Surgical sutures can be permanent or temporary, and can be made of degradable or non-degradable materials depending on the type of wound. Permanent, or non-degradable, sutures are typically used for closing a skin wound, and may be removed after the wound heals. Permanent sutures can also be used internally for applications that require strong mechanical support for the tissues over a long period of time. In contrast, temporary sutures, which are biodegradable, are used for smaller wounds that exhibit a faster healing time. Depending on the severity and location of the wound, the number of sutures used, and surgical techniques that are practiced, some surgical sutures may experience a large tensile force that may cause them to fail or further tearing of the tissue.

A number of sensors have been designed for monitoring forces and other conditions at wound sites during and after surgery. For example, stitch-force sensors and hook-force sensors monitor the tension of a suture prior to wound closure. The sensor systems can guide surgeons to apply the correct tension on the suture. The correct amount of tension is important because an excessively tight suture can lead to ischemia of tissue and a loose suture is unable to provide a proper mechanical support for the wound. Although such sensors are accurate, they cannot be used to monitor wound conditions, including tension on the suture, postoperatively.

A flexible sensor system, made of integrated single crystal silicon nanomembrane electronics, can be incorporated within a suture to monitor pressure and temperature and to generate heat in the area around the suture. However, this sensor is not designed to monitor the tensile force on the suture. Rather, this sensor monitors the conditions near the wound site. In addition, this sensor requires direct connection to a power supply and data acquisition system, which prevents it from long-term monitoring of a suture at a closed wound.

The ability to track conditions of orthopedic injury sites is very useful for improving treatment outcomes. Current sensor technologies do not allow for real-time tracking of internal injury sites. Standard sensors cannot directly measure stress and/or strain at internal muscles or tendons, while imaging methods such as magnetic resonance imaging, x-ray, and ultrasound cannot be deployed accurately while in motion or around metallic implants.

It would therefore be desirable to have a system and method to provide for postoperative in vivo monitoring of mechanical forces. Such a system may prevent excessive force from damaging the wound repairs and may be used to gain useful information for improving surgical techniques for wound repair as well as in post-operative care.

SUMMARY

The present invention provides a system and method for monitoring mechanical forces applied to a wound site repairing structure.

In one aspect, a system is provided for monitoring a mechanical force applied to the wound site repairing structure. The system includes a wound site repairing structure, a magnetoelastic sensor coupled to the wound site repairing structure, and a detection system. The detection system includes an excitation coil configured to transmit a signal to the magnetoelastic sensor, a detection coil constructed and arranged to generate a signal indicative of a mechanical force applied to the wound site repairing structure, and a detection unit configured to detect the signal indicative of the mechanical force applied to the wound repairing structure. In another aspect, the detection system includes an electrical current generator configured to generate an electrical current in the excitation coil to thereby transmit the signal to the magnetoelastic sensor and the signal produced by the detection coil is indicative of a change in the magnetic permeability of the magnetoelastic sensor when the mechanical force is applied to the wound site repairing structure.

In another aspect, the signal produced by the detection coil includes one of a voltage or a current in the detection coil. In yet another aspect, the detection system includes a power source configured to generate an electrical current in the excitation coil. In a further aspect, the magnetoelastic sensor is structured so as to be located in an in vivo environment. In an additional aspect, the signal indicative of a mechanical force includes a signal indicative of a force between about 0.1N and 1.5N applied to the wound repairing structure. In still another aspect, the signal indicative of the mechanical force is a signal indicative of a force between about 1.5N and 44.5N applied to the wound repairing structure.

In yet another aspect, the wound repairing structure includes a substrate, the magnetoelastic sensor coupled to the substrate. In another form, the wound repairing structure includes a first suture, a second suture, and a substrate having a first end attached to the first suture, and a second end attached to the second suture. In yet another form, the wound repairing structure includes a first suture including a first loop, a second suture including a second loop, and a substrate including a first hook coupled to the first loop of the first suture, and a second hook coupled to the second loop of the second suture. In another form, the detection unit includes a current or volt detector that detects a current or voltage induced in the detection coil. In still another form, the excitation coil is configured to generate an alternating current magnetic field so as to generate the signal transmitted to the magnetoelastic sensor.

In another aspect, the excitation coil is concentric with the detection coil, and a diameter of the excitation coil is larger than a larger diameter of the detection coil. In another aspect, the wound repairing structure includes a bone anchor and a suture coupled to the bone anchor. In still another form, the magnetoelastic sensor includes a biodegradable material. In additional forms, the wound repairing structure includes a suture, and the magnetoelastic sensor includes a magnetoelastic coating disposed along the suture.

In yet another form, an enclosure surrounds the magnetoelastic sensor to protect the sensor from a surrounding environment. In another form, the wound repairing structure includes a bone anchor, a fixation rod and a suture. The fixation rod and suture are coupled to the bone anchor. A magnetoelastic sensor is attached to the bone anchor. In another form, the wound repairing structure includes a bone anchor, a fixation rod coupled to the bone anchor, and a suture coupled to the fixation rod, wherein the magnetoelastic sensor is attached to one of the fixation rod or the suture.

In an additional aspect, a method is provided for monitoring a mechanical force applied to a wound site repairing structure. The method includes transmitting a signal from through an excitation coil to a magnetoelastic sensor coupled to wound site repairing structure, producing, at a detection coil, a signal indicative of a mechanical force applied to the wound site repairing structure, and detecting the signal indicative of the mechanical force applied to the wound site repairing structure.

In another aspect, the transmitted signal includes a magnetic field. In an additional aspect, the method includes generating an alternating current in the excitation coil so as to produce the signal transmitted from the excitation coil to the magnetoelastic sensor. In yet a further aspect, the mechanical force applied to the wound site repairing structure is a tensile force.

Various other features of the present invention will be made apparent from the following detailed description and the drawings.

BRIEF DESCRIPTION OF THE DRAWINGS

FIG. 3 illustrates another embodiment of a wound site repairing structure in a force monitoring system of the present disclosure in which the structure includes a bone anchor.

FIG. 3A illustrates another embodiment of the wound site repairing structure of FIG. 3 in which at least one sensor is coupled to the bone anchor and/or to a fixation rod of the bone anchor.

FIG. 3B illustrates another embodiment of the wound site repairing structure of FIG. 3 in which a sensor is coupled to the bone anchor.

DETAILED DESCRIPTION

Figure 1A:
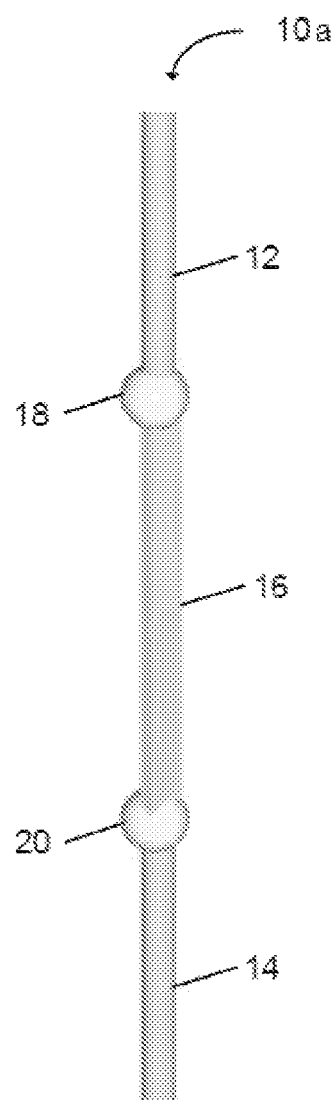
FIG. 1A illustrates an embodiment of a wound site repairing structure and a sensor coupled to the structure in a force monitoring system of the present disclosure.
Figure 1B:
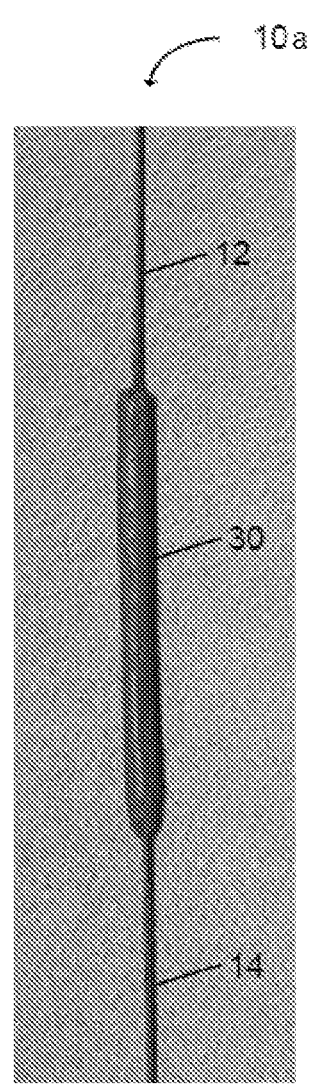
FIG. 1B illustrates the wound site repairing structure and sensor of FIG. 1A having a protective enclosure or coating surrounding the structure.

FIGS. 1A and 1B illustrate an embodiment of a wound site repairing structure 10a and a magnetoelastic sensor 16 coupled to the structure 10a. Wound site repairing structure 10a is structured so as to be deployed to an in vivo environment to repair bone, muscle, tissue, or in any other biological environment such as skin. Structure 10a includes a first suture 12 and a second suture 14, each of which can be attached to a biological environment to aid in repairing a wound site. Sutures 12 and 14 in one example are conventional medical sutures like Ethicon's Coated Vicryl® Polyglaticn 910 suture. Magnetoelastic sensor 16 includes a thin magnetoelastic strip of metal (e.g., a 30 mm×1 mm strip of Metglas® 2826 MB, an amorphous ferromagnetic alloy). An end 18 of first suture 12 is coupled to sensor 16 via adhesion, and a second end 20 of sensor 16 is coupled to second suture 14 via adhesion. Sensor 16 can be arranged within a protective enclosure or coating 30 to protect sensor 16 from the surrounding environment. In an embodiment, protective enclosure or coating 30 can include any biocompatible material, e.g., a polymer or metallic material. It should be appreciated, however, that enclosure 30 can be made of any material suitable for use with a biological environment and capable of protecting the sensor 16. In one example, coating 30 comprises rubber.

By coupling sensor 16 to suture threads 12 and 14, sensor 16 is able to sense mechanical or tensile forces applied to one or both of suture threads 12, 14 (e.g. forces occurring from person's tissue, muscle or skin at a wound site). That is, when structure 12 is secured to a wound site, mechanical or tensile forces applied to first 12 and/or second 14 sutures can be transferred from the wound site to the sensor 16, which causes a change in the magnetic response or permeability of sensor 16. It should therefore be appreciated that magnetoelastic sensor 16 can be any type of magnetoelastic sensor or material capable of exhibiting a change in magnetic properties when a mechanical stress or strain is applied to the material or sensor. For example, sensor 16 can be a coating that exhibits magnetoelastic properties instead of a thin magnetoelastic metallic strip as illustrated in FIG. 1. It should further be appreciated that the wound site repairing structure 10a and sensor 16 illustrated in FIG. 1 allow sensor 16 to sense smaller forces applied to the wound site repairing structure 10a, for example, less than 1.5 Newtons (N).

Figure 1E:
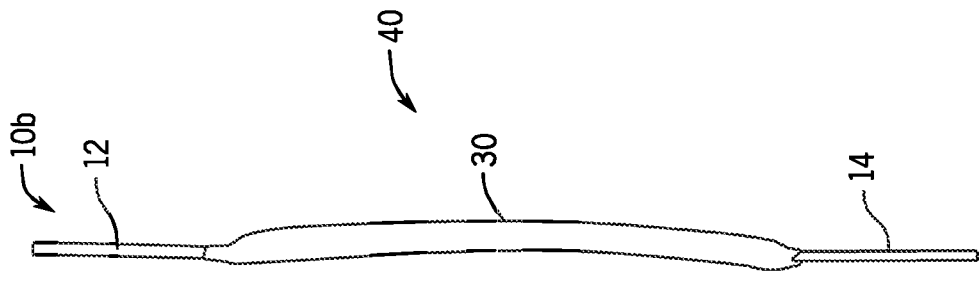
FIG. 1E illustrates the wound site repairing structure and connecting unit of FIGS. 1C and 1D having a protective enclosure or coating surrounding the structure.
Figure 1D:
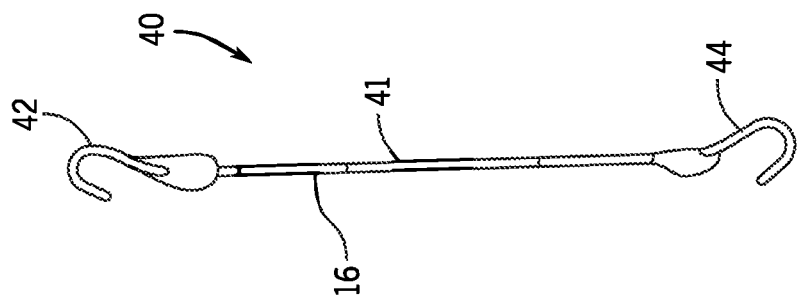
FIG. 1D illustrates an embodiment of a connecting unit of the wound site repairing structure of FIG. 1C.
Figure 1C:
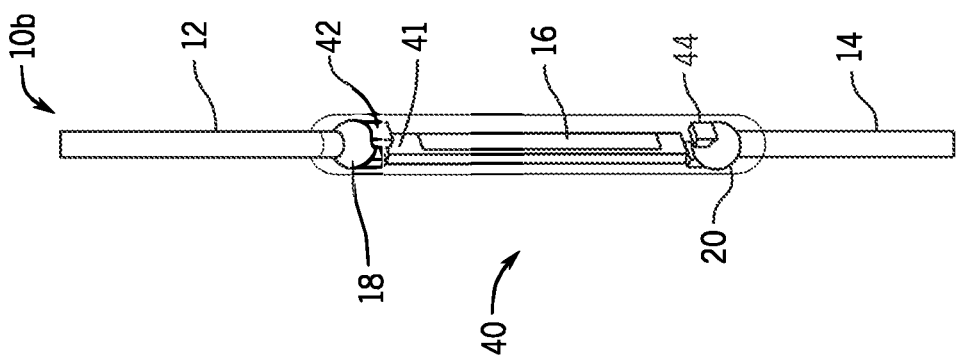
FIG. 1C illustrates another embodiment of a wound site repairing structure in a force monitoring system of the present disclosure in which the structure includes a connecting unit to which the sensor is coupled.

FIGS. 1C to 1E illustrate another embodiment of a wound repairing structure 10b having a magnetoelastic sensor 16 coupled to the structure 10b. Here, instead of sensor 16 being directly coupled to the sutures 12 and 14 like the embodiment of FIGS. 1A and 1B, structure 10b includes a connecting unit 40 to which sensor 16 is coupled (e.g., coupled by adhesion). Connecting unit 40 includes a substrate 41 having first 42 and second 44 connecting elements disposed at opposite ends of the substrate 41. Substrate 41 is formed with hooks 42, 44, as illustrated in FIG. 1D. Loops or knots are formed in the ends 18, 20 of sutures 12 and 14, respectively, to couple the hooks 42, 44 to their respective knots or loops. It should be appreciated that connecting elements 42, 44 and their cooperating suture attachments structures can be any suitable coupling or attachment means including clips, clasps or adhesives.

Sensor 16 in FIGS. 1C to 1E is made of any suitable thin magnetoelastic strip or coating like sensor 16 of FIGS. 1A and 1B. Substrate 41 is formed of a material that is thicker than sensor 16. In one example, substrate 41 is a metal strip having dimensions of about 28 mm×1 mm×0.5 mm, while sensor 16 is 20 mm×1 mm×0.5 um. Coupling sensor 16 to a substrate that is thicker than the sensor, instead of directly to sutures 12 and 14 like the embodiment of FIGS. 1A and 1B, allows the substrate to experience most of the mechanical or tensile forces applied from the wound site to the sutures 12 and 14. Sensor 16 in FIGS. 1C to 1E therefore experiences only a fraction of an applied load, resulting in a larger force being sensed or detected by sensor 16. Thus, the configuration of FIGS. 1C to 1E, allows sensor 16 to measure higher loading forces than the configuration illustrated in FIGS. 1A and 1B, for example, between 1.5N and 44.5N.

Figure 2:
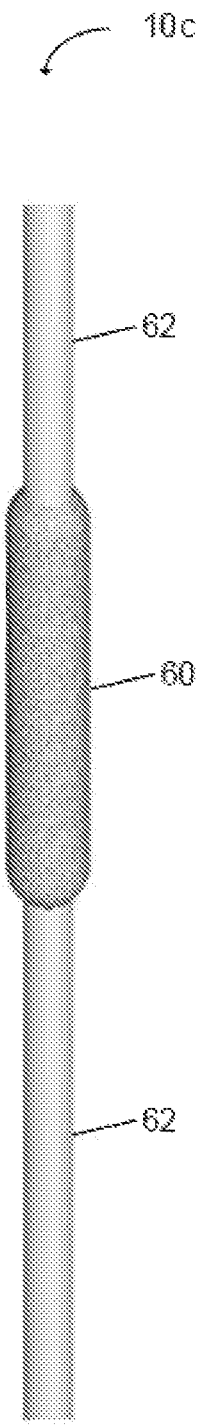
FIG. 2 illustrates another embodiment of a wound site repairing structure in a force monitoring system of the present disclosure in which the structure includes a suture having a magnetoelastic coating sensor coupled to the suture.

FIG. 2 illustrates another embodiment of a wound repairing structure 10c. Here, structure 10c includes a sensor coating 60 applied to a section of a single suture 62. Sensor coating 60 like sensors 16 above, can be comprised of any suitable magnetoelastic material which produces a change in magnetic properties (e.g., magnetic permeability) when a force is applied to the coating 60. Suture thread 62 and coating 60 of FIG. 2 (along with sutures 12 and 14 and sensor 16 of FIGS. 1A to 1E) can also comprise a bioabsorbable and/or biodegradable material such that the suture 62 and coating 60 degrade within the body, eliminating the need for removal of the suture. For example, sensor coating 60 may be made of an iron-gallium material, $Fe_{88}Ga_{12}$ or $Fe_{71}Ga_{29}$. Sensor coating 60 may also be applied to other wound repairing structures, such as bone anchors and/or fixation plates.

In some embodiments, sensor coating 60 operates similar to sensors 16 such that when a mechanical or tensile force is applied to the sensor coating 60, one or more magnetic property of the sensor coating 60 is altered. When the one or more magnetic property of the sensor coating 60 is altered, detecting means can detect and relay that information to a controller or a computing device as described below. It should be appreciated from the foregoing that that either the thin strip of material or a sensor coating, can be used for the magnetoelastic sensors of the present disclosure. Sensor coating 60 may be desirable for use when it is difficult to implant a strip of magnetoelastic material, or for any other purpose.

FIGS. 3, 3A, and 3B illustrate a wound repairing structure 10d having a bone anchor 66 and suture 62 and a magnetoelastic coating or sensor 60 coupled to the structure 10d. Bone anchor 66 is anchored to a bone 68, and suture 62 connects the bone anchor 64 to a tendon or tissue 70 that is normally in connection with the bone 68. Bone anchor 64 and suture 62 are structured to repair a damaged rotator cuff. However, bone anchor 64 and suture thread 62 may be used to connect any bone and/or soft tissue (e.g., tendon or ligament) with any other bone or soft tissue.

In one configuration, suture 62 is coupled to fixation rod 64 of bone anchor 66, as illustrated in FIG. 3A. Coating 60 can be applied to one or more of suture 62 or fixation rod 64. In an embodiment, the entire length of fixation rod 64 can include a magnetoelastic stress-sensitive material. In this configuration, a load on suture thread 62 generates a stress on the fixation rod 64, resulting in a change in the signal from the fixation rod 64.

In another configuration, suture thread 62 is coupled directly to the bone anchor 76 as illustrated in FIG. 3B. Here, a magnetoelastic sensor or coating 60 can be applied to a tab 72 extending from the bone anchor 76. It should be appreciated that tab 72 and bone anchor 76 may be formed as one-piece or be separate pieces coupled together by any one of threading, snap fit, interference fit, or any other suitable mechanical coupling method known to those of ordinary skill in the art. The magnetoelastic sensor or coating can be applied to a side of tab 72. In some embodiments, the sensor or coating is applied to a side of the tab 72 to detect a tensile stress or strain applied to tab 72 due to the positioning of the suture thread 74 at an end of the tab 72.

Figure 4A:
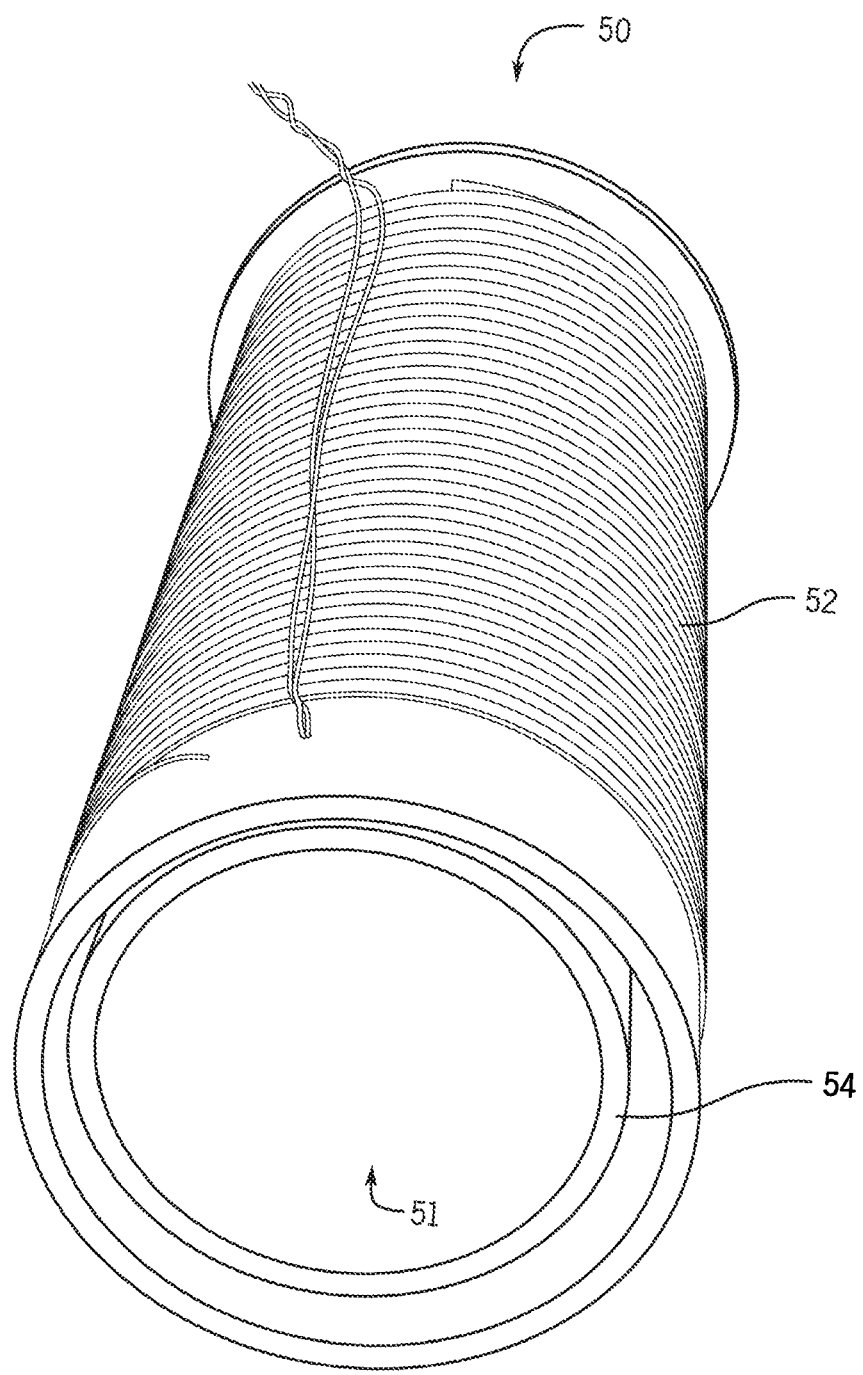
FIG. 4A illustrates an embodiment of a detection system of the force monitoring system of the present disclosure.

Referring now to FIG. 4A, FIG. 4A illustrates a detection system 50 that communicates with sensors 16 or 60 so as to detect a signal indicative of the mechanical or tensile force applied to a wound site repairing structure (e.g., structures 10a to 10d). Detection system 50 includes an excitation coil 52 that surrounds a detection coil 54 such that coil is 52 is arranged substantially concentric to coil 54 and has a larger diameter than coil 54. In the illustrated example, coil 52 is wrapped around a first cylindrical drum, while coil 54 is wrapped around a second cylindrical drum. The second drum defines an interior volume or passage 51 structured so as to at least partially surround both the wound repairing structure (e.g., structures 10a to 10d described above) and the magnetoelastic sensors coupled to the structures (e.g., sensors 16 or 60 described above). It should be appreciated that sensors 16 or 60 do not need to be located directly within passage 51.

A detection unit (not shown in FIG. 4A) communicates with the detection coil 52 to detect a signal indicative of the mechanical force applied to the wound site repairing structure. In one example, the detection unit includes a signal reader such as a voltage or current meter that detects the voltage or current induced in detection coil 54. Detection system 50 also includes a power source or signal generator (not illustrated) to generate a signal in the excitation coil.

Detection system 50 operates generally by a power source or signal generator generating an electric current in excitation coil 52. Detection coil 54 detects a signal indicative of a force or load applied to the wound repairing structure, which results from sensor 16 or 60 being coupled to the structure. The signal detected by the detection system can include one of a voltage, a current, or a magnetic signal. In particular, the detection system 50 monitors the change in magnetic permeability of sensor 16 to produce a feedback signal related to the force applied to the wound site repairing structure. For example, the detection system 50 can monitor a feedback signal at a frequency that is an integer multiple of the excitation magnetic field frequency. The separation in excitation and detection frequencies allows for increased amplification of the sensor signal without amplifying the excitation field, resulting in a larger signal-to-noise ratio. In the following examples, the $3^{rd}$ order harmonic frequency was used because it has a large signal amplitude among the harmonic frequencies at zero biasing fields.

In particular, detection system 50 can monitor sensor magnetization at harmonic frequencies with the detection coil 54. It should be appreciated that because there does not need to be direct contact between the sensors (e.g., sensors 16 or 60) and the detection system, the force monitoring system of the present disclosure can be used for in vivo, real-time tracking of force loading on the wound repairing structure post-operation, even when the wound repairing structure is located inside a person's body.

In one example of detections system 50, excitation coil 52 of includes a solenoid that is 80 mm in length and 40 mm in diameter. The solenoid has 220 turns, and includes 26 gauge magnet wire. The detection coil 54 includes two solenoids connected in series, but with opposite winding directions to cancel out majority of the excitation signal in the absence of sensor 16. Each detection coil 54 is 38 mm in length and 33 mm in diameter. In addition, each detection coil 54 has 172 turns, and includes 32 gauge wire.

In another example of the detection system, excitation coil 52 is a solenoid having a length of 80 mm and a diameter of 115 mm. The solenoid has 205 turns, and includes 20 gauge wire. Detection coil 54 includes two solenoids connected in series but with opposite winding directions to cancel out majority of the excitation signal in the absence of sensor 16. Each detection coil 54 is 35 mm in length and 105 mm in diameter. In addition, each detection coil 54 has 150 turns, and includes 32 gauge wire.

Figure 4B:
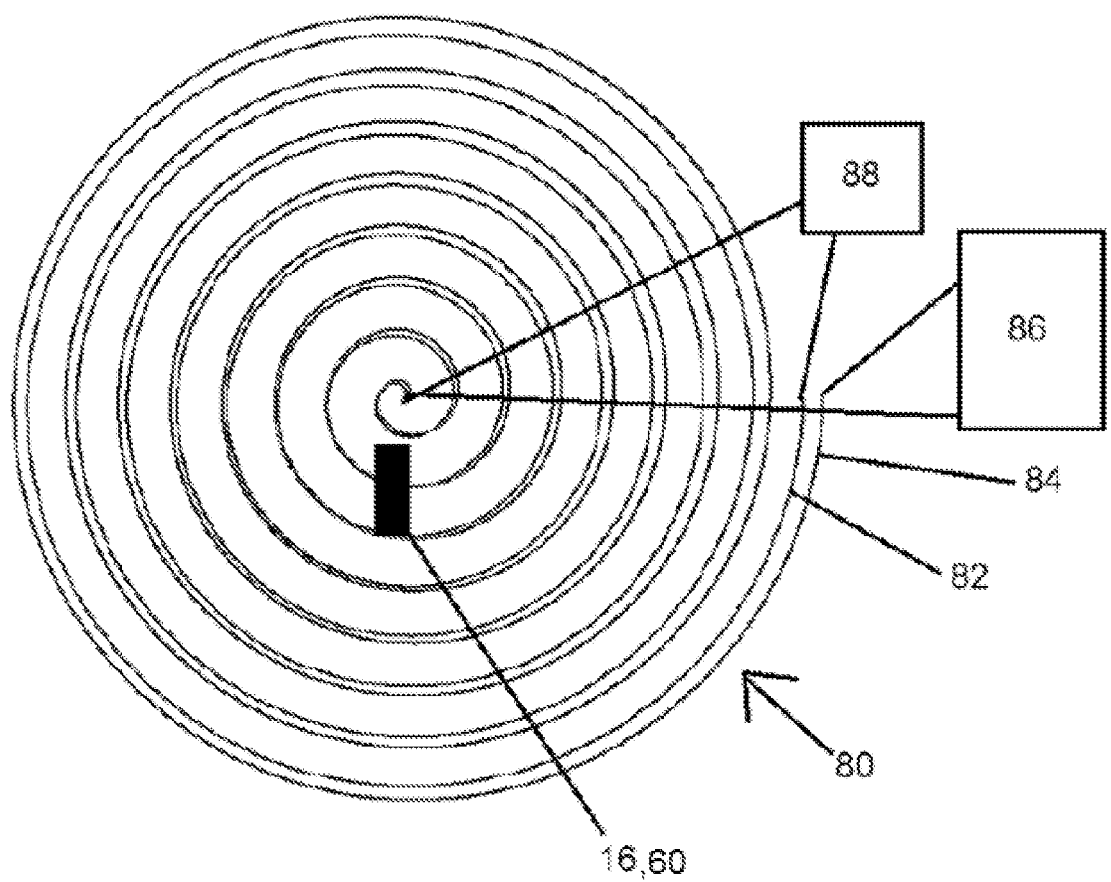
FIG. 4B illustrates another embodiment of a detection system of the force monitoring system of the present disclosure.

FIG. 4B is a schematic illustration of another embodiment of a detection system 80 that communicates with a magnetoelastic sensor (e.g., sensors 16 or 60) so as to detect a signal indicative of the mechanical or tensile force applied to a wound site repairing structure (e.g., structures 10a to 10d). Here, the excitation coil 82 and the detection coil are arranged in a planar configuration instead of a concentric configuration like FIG. 4A. In particular, excitation coil 82 and detection coil 84 are wound in a spiral or circular like formation and located in either the same plane or in parallel planes (e.g., on a single substrate or on respective parallel substrates). The planar coils 82, 84 can overlie the wound repairing structure (e.g., structures 10a to 10d above) and the sensor coupled to the structure (e.g., sensors 16 or 60). A power source or signal generator illustrated schematically in FIG. 4B as excitation circuit 88, communicates with the excitation coil 82 so as to generate a signal in the excitation coil 82. Detection coil 84 communicates with a detection unit which is likewise illustrated schematically as detection circuit 86 in FIG. 4B. When an AC current is passed through the excitation coil 82, and a change in the magnetic properties of sensor 16 are detected by detection coil 84 as a result of a stress or strain being applied to the wound repairing structure and hence the sensor 16 attached to the structure.

It should be appreciated that detection coils described herein can include two multi-turn coils of equal turn numbers wounded in opposite directions (one clockwise and the other counterclockwise). The two coils are connected in series to cancel out the signal from the excitation coil so all signals captured at the terminals of the coils are solely signals from the magnetoelastic sensor. It should further be appreciated that the sensor disclosed herein produces a magnetic field and the signal mechanical force is indicated by measuring the perturbation of the voltage or electrical impedance across the excitation coil. It should further be appreciated that in an alternative example of the force monitoring system of the present disclosure, the system operates without a detection coil and instead uses an excitation coil and a detection unit. The detection coil in this example is configured to transmit a signal to the magnetoelastic sensor, while the detection unit is configured to measure the change in the excitation coil (e.g., voltage, current, impedance), which is indicative of the mechanical force applied to the wound site repairing structure.

Figure 5:
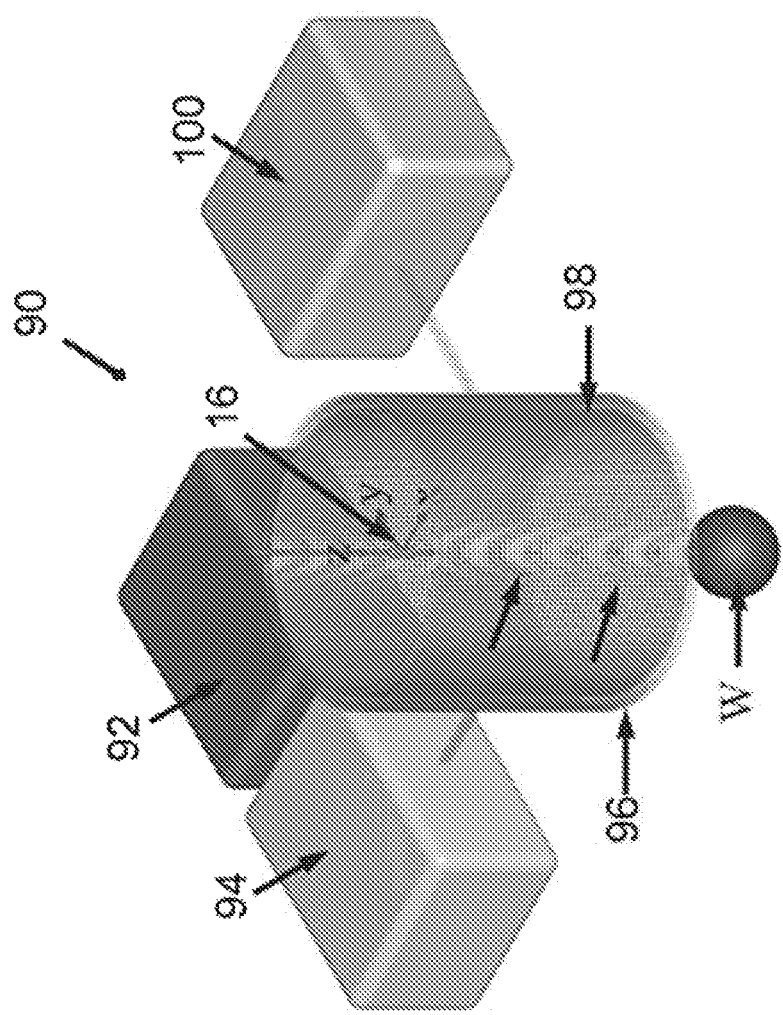
FIG. 5 illustrates an experimental testing system for monitoring a force applied to a wound repairing structure for use in a force monitoring system of the present disclosure.

Referring now to FIG. 5, FIG. 5 illustrates an experimental testing system 90 for monitoring the force applied to a wound repairing structure (e.g., a suture) in accordance with the principles of the present disclosure. System 90 includes a function generator 92, an amplifier 94, an excitation coil 96, a detection coil 98, and a detection unit or spectrum analyzer 100. Function generator 92 is configured to generate an electrical current in excitation coil 96. Sensor 16 is coupled to a weight W, which mimics the forces that would be applied to a wound site repairing structure that is secured to a patient wound site. The function generator 92 operates to send a signal (e.g., a current) to the amplifier that amplifies the signal. The signal is sent to the excitation coil 96 which operates as a solenoid. The excitation coil 96 acts as a solenoid generating a magnetic field that is formed from within the center of excitation coil 96. When the weight W is applied to sensor 16, the magnetic field is transmitted to the sensor 16 and a signal can be tracked and analyzed by spectrum analyzer due to the change in magnetic permeability of sensor 16. Spectrum analyzer 100 can include a controller, a processor, or a computing device.

In one example test set-up of detection system 90, sensor 16 was energized with a 200 Hz magnetic AC field using a Fluke 271 function generator and Tapco J1400 amplifier through the excitation coil 52. Sensor 16 was magnetized at 600 Hz and tracked at different weight loadings using an Agilent spectrum analyzer (4396B) via detection coil 54. A computer was connected to the spectrum analyzer to control the experiment and collect measurements for data processing.

Figure 6A:
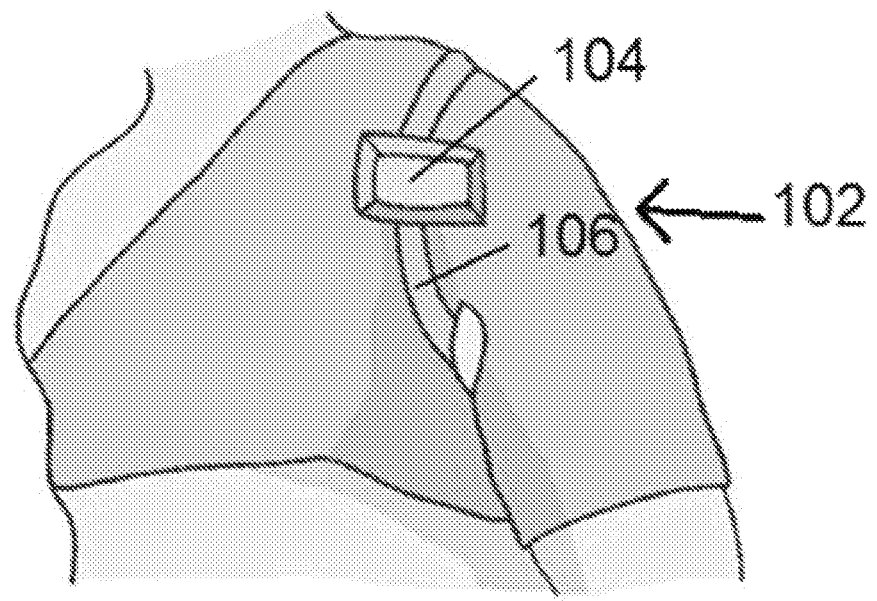
FIG. 6A illustrates an embodiment of a detection system of a force monitoring system of the present disclosure in which the detection system is coupled to a patient's shoulder.

Referring now to FIG. 6A, FIG. 6A illustrates an example of a detection system 102 of the present disclosure. The detection system of FIG. 6A is coupled to a patient's shoulder so as to detect and monitor a force applied to a wound site repairing structure (not shown). The wound site repairing structure is not shown in FIG. 6A because the structure is located in vivo or internal to the patient's body (e.g., wound site repairing structure 10d that is used to repair a rotator cuff as discussed above). Detection system 102 includes an excitation coil 106 and a detection coil (not shown) disposed concentric with coil 106. It should be appreciated that the excitation coil and detection coil 106 can be disposed on a cylindrical structure and arranged substantially concentrically as discussed above. The detection system 102 also includes an electronics housing 104 that encloses or supports a power source or signal generator (not shown) that generates an electric current in an excitation coil 106. Electronics housing 104 also houses a detection unit (not shown) that detects the signal in the detection coil as described above. It should therefore be appreciated that detection system 102 operates like the detection systems described above, in that a signal or current is generated in the excitation coil 106, which produces a magnetic field signal. The magnetic filed signal is transmitted to the sensor located internal to the patient's body, allowing the sensor to generate a secondary magnetic field, the magnitude of which is proportional to the mechanical force applied to the wound site repairing structure. The secondary magnetic field produces a voltage at the detection coil. The detection unit detects the signal produced in the detection coil, which is indicative of the force applied to the wound site repairing structure.

Electronics housing 104 can also include at least one controller, processor, or computing device to analyze and process signals of the detection system 102 (e.g., the signal detected by detection unit). A wireless transmitter (not shown) can also be included in the electronics housing 104 to transmit wirelessly the signals that are detected by the detection unit to a computer, or smart devices (smartphones, smart-watches, and other wearable electronics) for real-time data reading/analysis and long-term storage. In other embodiments, electronics housing 104 can include a display that operates with a processor to display the amount of force acting on the wound site repairing structure.

Figure 6B:
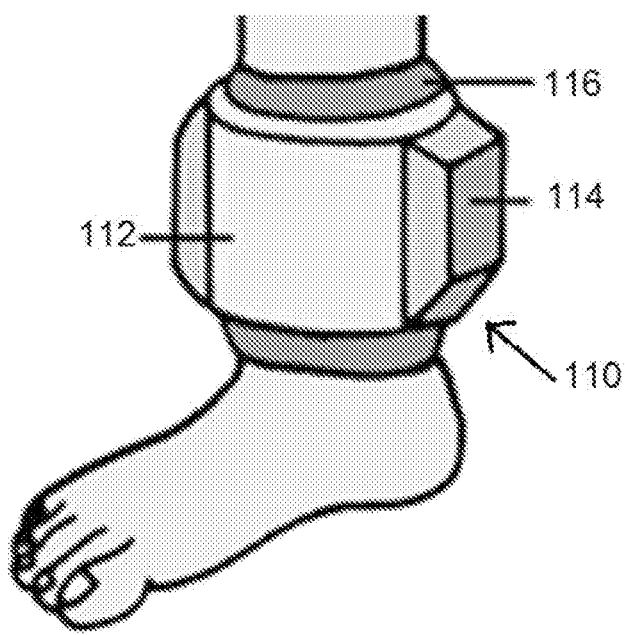
FIG. 6B illustrates another embodiment of a detection system of a force monitoring system of the present disclosure in which the detection system is coupled to a patient's leg.

FIG. 6B illustrates another example of a detection system 110 of the present disclosure. Here, the detection system 110 is coupled to a patient's leg so as to detect and monitor a force applied to a wound site repairing structure (not shown). The wound site repairing structure is again not shown in FIG. 6B because the structure is located in vivo or internal to the patient's body (e.g., wound site repairing structure 10d that is used to repair a rotator cuff as discussed above). Detection system 110 includes cylindrical housing structure that holds or supports an excitation coil (not shown) and a detection coil (not shown) in a generally concentric configuration. System 110 also includes an electronics housing 114 similar to FIG. 6A that encloses or supports a power source or signal generator (not shown) that generates an electric current in an excitation coil. Electronics housing 114 also houses or supports a detection unit (not shown) that detects the signal in the detection coil as described above. An inflatable bag 116 is located between the patient's leg and the housing 112 for ease of comfort and/or to protect the patient's wound site from damage. It should be appreciated that system 110 can operate without inflatable bag 116 and that inflatable bag 110 can instead any suitable structure or material that protects and provides comfort to the patient's leg (e.g., medical wrap, cloth, gauze, or any other material). Detection system 110 operates in the same or substantially the same way as the detection systems described above, in that a signal or current is generated in the excitation coil, which produces a magnetic field signal. The magnetic filed is transmitted to the sensor internal to the patient's body, which allows the sensor to generate a secondary magnetic field to the detection coil (not shown). The detection coil then produces a signal indicative of a change in the mechanical force applied to the wound site repairing structure, which is a change in the magnetic property or permeability of the sensor coupled to the structure.

Electronics housing 114 can also include at least one controller, processor, or computing device to analyze and process signals of the detection system 110 (e.g., the signal detected by detection unit). A wireless transmitter (not shown) can also be included in the electronics housing 104 to transmit wirelessly the signal detected by the detection unit to a computer or monitor, or smart devices (smartphone, smartwatches, and other similar wearables with wireless communication capabilities). In other embodiments, the electronics housing 104 can include a display that operates with the processor to process the signals detected by the detection unit and display the amount of force acting on the wound site repairing structure.

Figure 7:
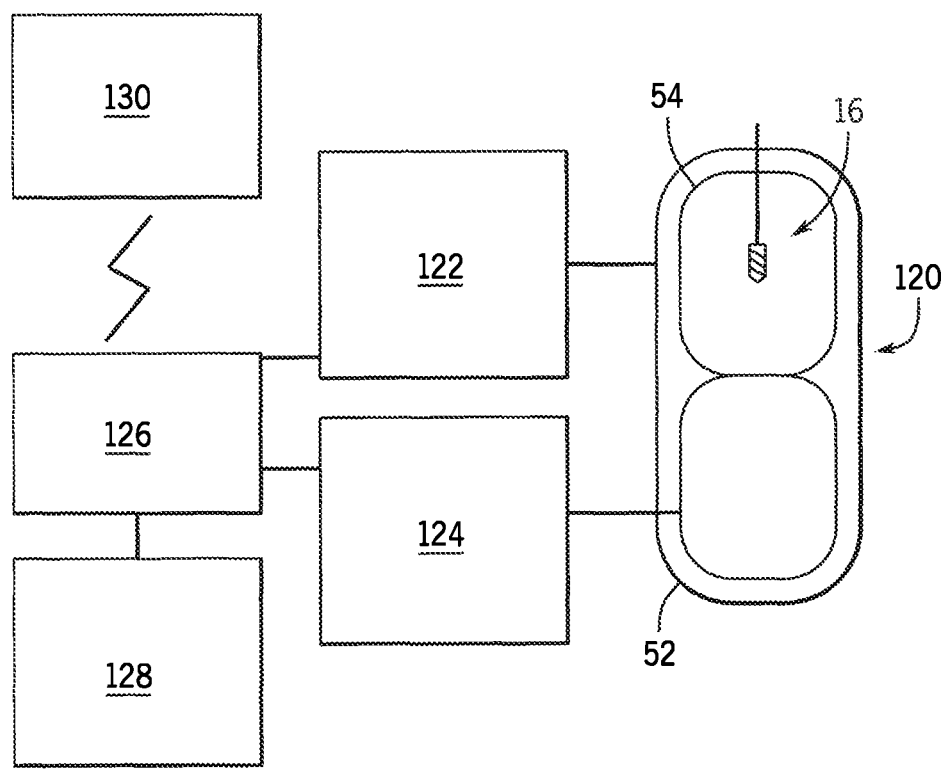
FIG. 7 is a schematic illustration of components of the force monitoring system of the present disclosure.

Referring now to FIG. 7, FIG. 7 is a schematic of various components 120 used in the force monitoring systems of the present disclosure. Components 120 include sensor 16 (or sensor 60), excitation coil 52, detection coil 54, excitation circuit 122, detection circuit 124, controller 126, and local data processing, storage unit or processor 128. It should be appreciated that sensor 16 is coupled to a wound site repairing structure as described above. Controller 126 can communicate via a wireless transmitter with a remote computer such as a smart phone 130 or other device outputs information so as to store, monitor and display the output of the force monitoring system to an end user (e.g., display the amount of force acting on wound repairing structure, or display that the amount of force exceeded a threshold amount and likely cause the wound repairing structure to rupture or become detached from the wound site). Components 120 operate such that the excitation circuit 122 and detection circuit 124 allow one or more signals to pass to the controller 126. Controller can send the one or more signals to the processor 128, which processes the signal data and outputs a signal that can be transmitted to the wireless device such as a smart phone 130.

It should be appreciated from the foregoing that because sensor 16 or 60 does not require internal power to operate, magnetoelastic sensors 16 or 60 allow for miniaturization of the sensor 16 without compromising battery lifetime. Magnetoelastic sensors 16 or 60 can detect a mechanical or tensile force due to their magnetoelastic properties, (e.g., the magnetic permeability of the sensors change with an applied force). Because the sensor signal captured by detection system 50 is proportional to the magnetization of the sensor 16, and the magnetization of the sensor 16 is directly correlated to the magnetic permeability of the material of the sensor 16, the application of a mechanical or tensile force results in a change in the measured signal amplitude.

It should also be appreciated that sensor 16 may be designed for use permanent wound site repairing structures such as sutures, where sensor 16 is resistant to biodegradation for long term force monitoring. On the other hand, sensor 16 can be used with biodegradable wound site repairing structures (e.g., biodegradable sutures), so sensor 16 may or may not be biodegradable and may include a biocompatible magnetoelastic material. If biodegradable, sensor 16 may be bioabsorbable and implemented in a biodegradable suture. This eliminates the need to remove the sensor after use.

In one example, the degradation rate and biocompatibility of an iron-gallium material was evaluated. Single crystal ingots of $Fe_{88}Ga_{12}$ and $Fe_{71}Ga_{29}$ were grown, and annealed at 1000° C. for one week. Samples were collected by electrode discharge machining of the crystals, and mechanically sheared into blocks of about 1.2 mm in size and 17.25 mg average mass.

Biocompatibility was determined through cytotoxicity analysis. All samples used in these analyses were sterilized for 12 h with An74 Anprolene ethylene oxide prior to use. Samples were incubated in standard culture media at 37° C. for 28 days. Media was collected at 1, 7, and 28 day time points. Indirect cytotoxicity analyses were performed by culturing L929 fibroblasts cells (ATCC) at $2\times10^4$ cells cm-2 with media collected from the materials at a ratio of 10:1 with standard culture media for 48 h at 37° C. and 5% CO2. Cell washes were performed in phosphate buffered saline (Sigma) and Trypsin-EDTA (0.05% Trypsin/0.53 mM EDTA; Cellgro) was used to detach cells in preparation for experimental seeding. Fluorescent staining with Calcein-AM (Invitrogen) and Ethidium Bromide (Sigma) was used to determine live and dead cells, respectively, via an inverted Axiovert 200M (Zeiss) fluorescent microscope. Cell survival, defined as the number of live cells divided by the total number of cells, was quantified by performing direct cell counts.

To determine the degradation rate of $Fe_{88}Ga_{12}$ and $Fe_{71}Ga_{29}$, mass of the alloy samples were measured prior to incubation in standard culture media for 28 days. The mass of samples was then measured again at 7, 14, 21, and 28 day time points; media renewals were also performed at each of these time points. Cells cultured in conditioned media from the $Fe_{88}Ga_{12}$ and $Fe_{71}Ga_{29}$ samples showed no significant reductions in cell survival at any time points when compared to standard media controls. Additionally, the average cell survival was over 95% at every time point for both materials.

The degradation rate of the iron-gallium alloys was characterized to insure that these results were due to the biocompatibility of ions released from the iron-gallium alloys rather than a resistance to degradation. $Fe_{88}Ga_{12}$ and $Fe_{71}Ga_{29}$ degraded at rates of 0.0567 mg and 0.0346 mg per day, respectively. These rates corresponded to an effective ion concentration of 46.4 µM for $Fe_{88}Ga_{12}$ and 28.0 µM for $Fe_{71}Ga_{29}$ at 28 day points. This result indicates that ions from iron-gallium alloys for both compositions do not adversely affect cell viability at or below these concentrations.

In another experimental test of the detection systems of the present disclosure, a sensor was applied to a test sample made of the skin section of a pig's shoulder, about 10 cm×5 cm×1 cm in size. An artificial wound, about 3 cm in length and 4 mm in depth was created at the center of the skin sample with a surgical scalpel. The wound was then closed with an Ethicon Coated Vicryl® Polyglactin 910 suture. A sensor was sutured onto the sample across the wound. To evaluate the force monitoring capability of the sensor, a Micro-measurements Type W25013 strain gauge was used. The strain gauge was attached to a stainless steel metal strip. Suture threads were attached to both ends of the metal strip, and sutured onto the sample across the wound in parallel with the sensor.

The change in the strain gauge resistance was measured by connecting its terminals to a Wheatstone bridge circuit and measuring the change in the output voltage of the circuit. Prior to attaching the strain gauge onto the skin sample, a calibration curve was obtained by applying a known tensile force at the strain gauge and monitoring the voltage change at the output of the bridge circuit.

To monitor the sensor, the test sample was suspended from a support at one end so the sensor situated directly at the center of the detection coil. A weight was then applied to the other end of the sample to create a tensile force on the test sample. At different weight applications, the response of the sensor was measured simultaneously with the measurements from the strain gauge.

Figure 8:
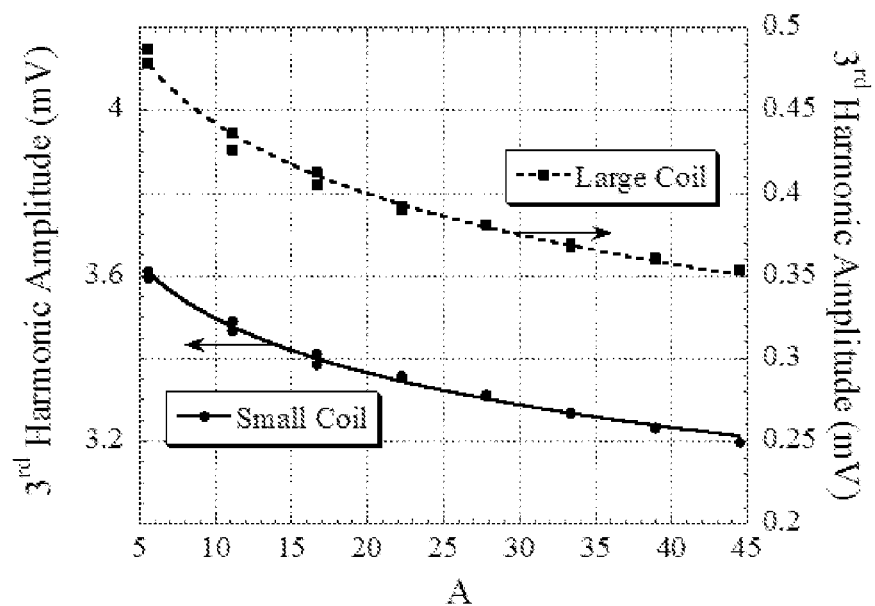
FIG. 8 is a graphical illustration of the change in a $3^{rd}$ harmonic field amplitude when a wound site repairing structure experienced a tensile force loading of up to 44.5 N.

Various loadings were applied to the test sample while measuring the output from the strain gauge setup and the amplitude signal from the sensor. The actual force at the strain gauge was calculated by calibrating the measured output voltage to the empirically obtained strain gauge calibration curve. The actual force measured by the sensor was determined by calibrating the measured field to the large coil curve as seen in FIG. 8.

Figure 9:
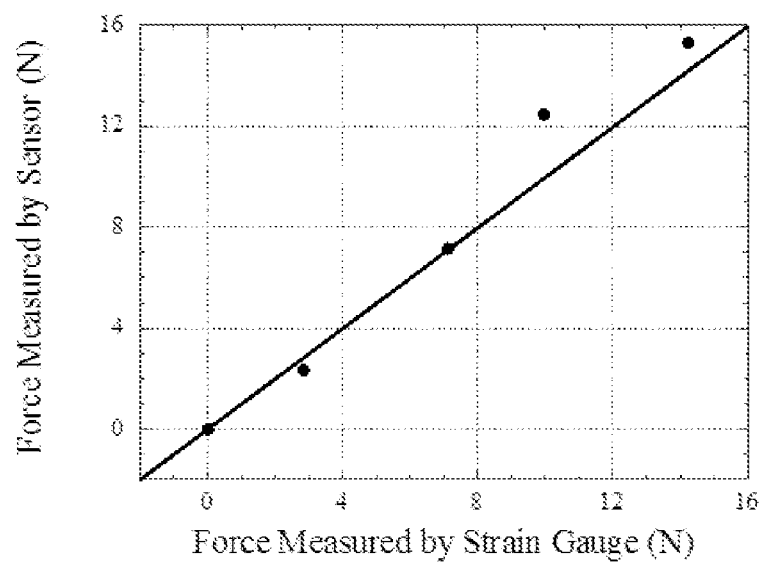
FIG. 9 is a graphical illustration of forces measured by the sensor compared to forces measured by a strain gauge when different loads were applied to a skin sample.

FIG. 9 shows plots of the measured force values of the sensor versus the force measurements of the strain gauge. Ideally, the curve should be linear with a slope of 1. The sensor showed a trend consistent with the strain gauge measurements, and only some differences were observed at higher force values. Because the sensor may be activated and monitored through magnetic fields, it can be used for in vivo force monitoring, such as monitoring of the tensile force on a suture after tendon and ligament repair. The ability of the sensor to directly monitor stress/strain of surgically repaired tissues such as tendons or muscles in situ and in real time can help to guide postoperative care or rehabilitations to prevent complications related to over stress. To evaluate the performance of the sensor inside tissue, a large-force sensor was embedded in the middle of a pig's shoulder tissue, about 10 cm×6 cm×6 cm in size, and placed inside the large coil. The signal from the sensor was the same compared to the signal when the sensor was alone.

The force monitoring system of the present disclosure was tested on a deer tendon (11 cm long×0.8 cm diameter) in another example testing system. Here, the sensor was sutured at two points along the length of the deer tendon with Ethicon's Coated Vicryl® Polyglaticn 910 sutures. The tendon was soaked in phosphate-buffered saline for six hours prior to testing to ensure that it was not stiff from dehydration. Additional sutures were placed at either end of the tendon to anchor the tendon to a hanging apparatus at the top and to applied weights at the bottom. A similar loading setup was implemented as the porcine skin test described above, and the change in the 3rd harmonic field from the sensor was monitored as the tendon was loaded with various tensile forces.

Figure 10:
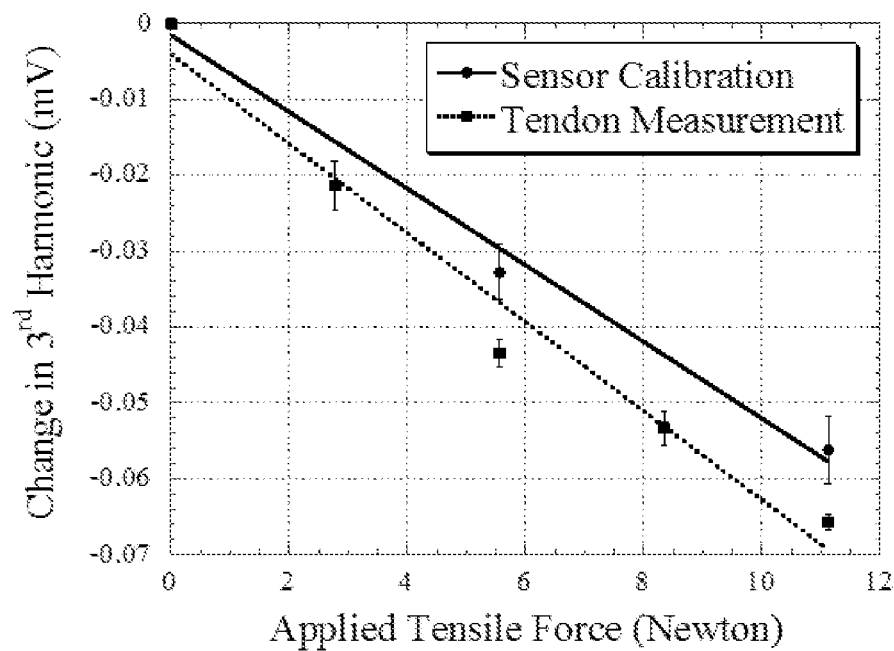
FIG. 10 is a graphical illustration of the 3rd harmonic amplitudes of the sensor when a dear tendon was loaded with a force ranging from about 0N to 12 N.

FIG. 10 is a graph illustrating the 3rd harmonic amplitudes of the sensor when a dear tendon was loaded with a force ranging from about 0N to 12 N. As the force increased, the 3rd harmonic amplitude of the sensor decreased, similar to the results in FIG. 8 The calibration of the sensor, obtained by measuring the sensor response while directly loading the sensor prior to suturing to the tendon sample, is also plotted in FIG. 10. Ideally, the calibration curve and the tendon-loading curve should match each other. The difference between these two curves may be due to the small stretching of the tendon sample at the suture anchoring sites when tensile force was applied.

Figure 11:
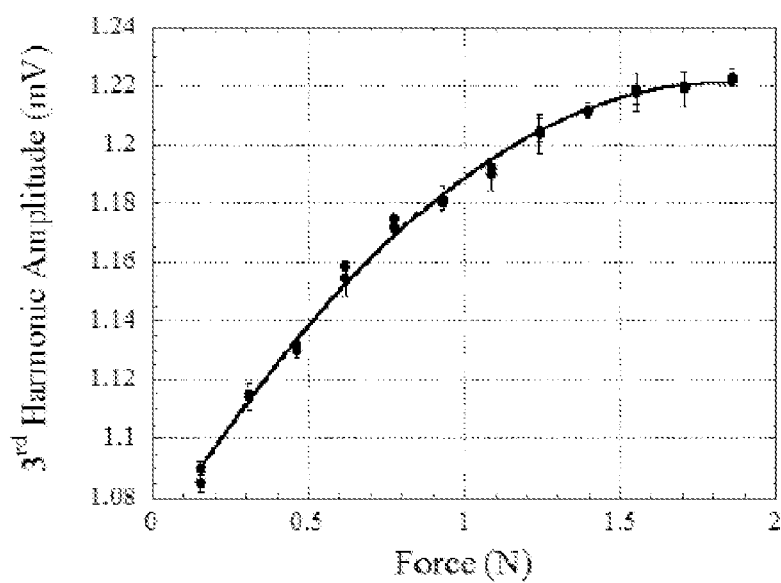
FIG. 11 is a graphical illustration of a change in the $3^{rd}$ harmonic field amplitude, measured with a small coil, when the sensor experienced a tensile force loading of up to 1.86 N.
Figure 12:
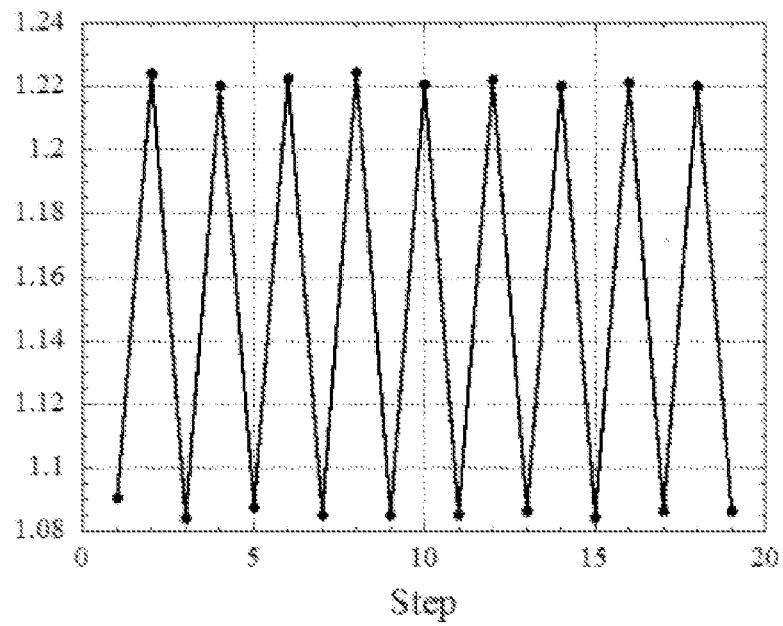
FIG. 12 is a graphical illustration of a sensor response measured with a small coil when the sensor was cycled between high load (1.86N) and low load (0.15 N) for over 9 cycles.

FIG. 11 is a graph illustrating the changes in the 3rd harmonic field amplitude measured with a small coil when a tensile force was applied to a low-force sensor. The results indicate an almost linear increase at forces below 1 N, but the increase slowed down significantly and saturated at about 1.5 N. Therefore, the sensor was suitable for only monitoring small force loading. The full scale of the sensor was about 0.14 mV (0.15N-1.5 N), or about 13% of the sensor signal at its lowest loading. FIG. 12 plots the change in the low-force sensor signal using both the small coil and the large coil when repeatedly cycled between 0.15N and 1.86 N. There was no observable drift during acquisition of this data.

Referring again to FIG. 8, the graph illustrates the 3rd harmonic field amplitude of the high-force sensor when it was loaded from 5.6N to 44.5 N, and then back to 5.6N using both the small coil and large coil. The results indicate that application of a tensile force on the sensor strained the stainless steel strip, which in turn generated a force on the magnetoelastic sensor through its adhesive joints. As a result, in addition to the tensile force, the sensor also experienced a large bending force. This caused the response of the sensor 16 to decrease instead of increase. The magnetic properties of the sensor 16 showed a logarithmic response, where its sensitivity decreased at increasing forces.

Figure 13:
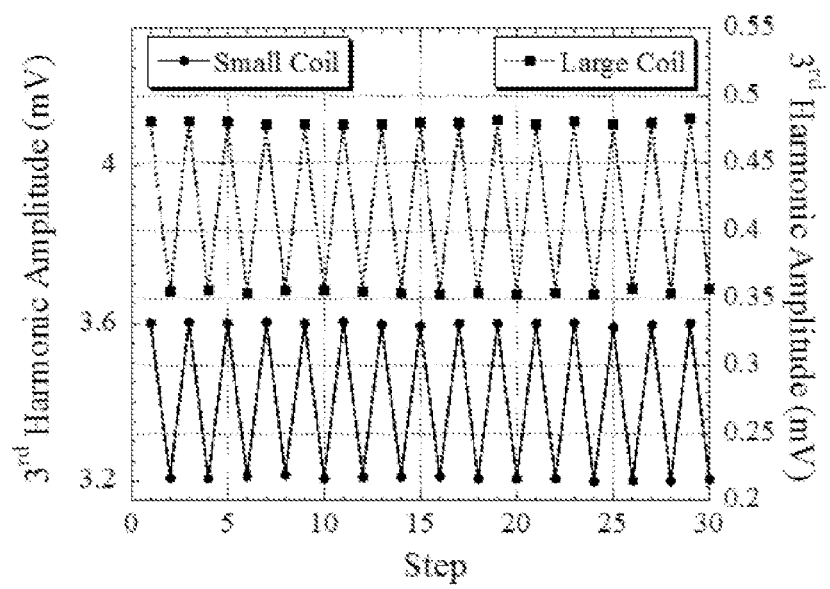
FIG. 13 is a graphical illustration of the response of the sensor measured with a small coil and a large coil when cycled between high load (44.5N) and low load (5.6 N) for over 15 cycles.

When monitored with the small coil, the full scale output of the high-force sensor was 0.4 mV, or about 12% of the sensor signal at maximum load. When using the large coil, the full scale output of the sensor was 0.125 mV, or about 37% of the sensor signal at maximum load. The hysteresis of the sensor signal was also determined from FIG. 8 as smaller than 3.5% of the sensor's full scale output for both coils. FIG. 8 indicates that monitoring the sensor with a larger coil reduces the signal amplitude by about 10 times, however, during the experiment, the full scale output of the sensor was increased by 3 times. In addition, experiments conducted with the large coil indicated that the large coil is a more practical size for use in large animals and humans. To examine the long term stability of the sensor, the sensor response was also monitored when it was cycled between 5.6N and 44.5N as recorded in FIG. 13. The signal drifts measured by the large and small coils were found to be less than 3%.

Figure 14A:
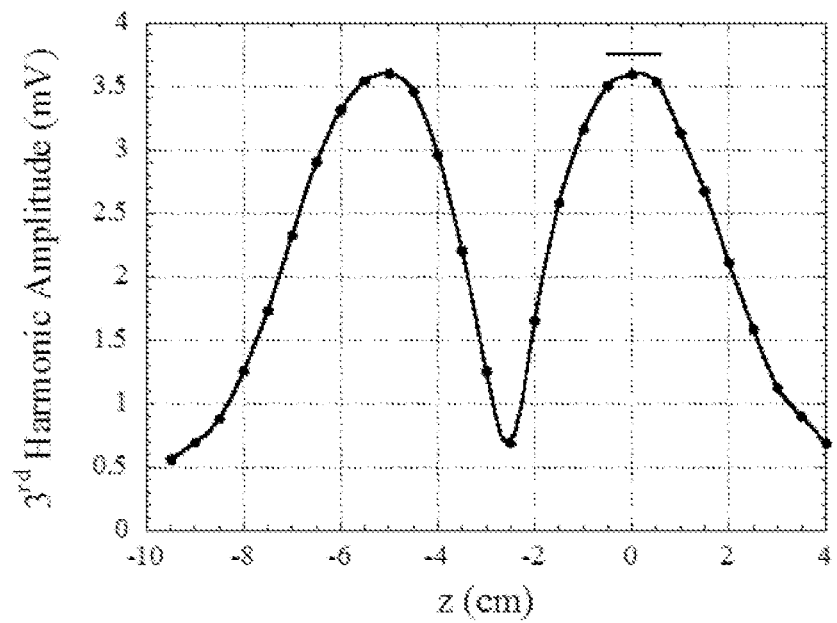
FIG. 14A is a graphical illustration of the change in the $3^{rd}$ harmonic amplitude when the sensor was moved along the z-axis of the small coil.
Figure 14B:
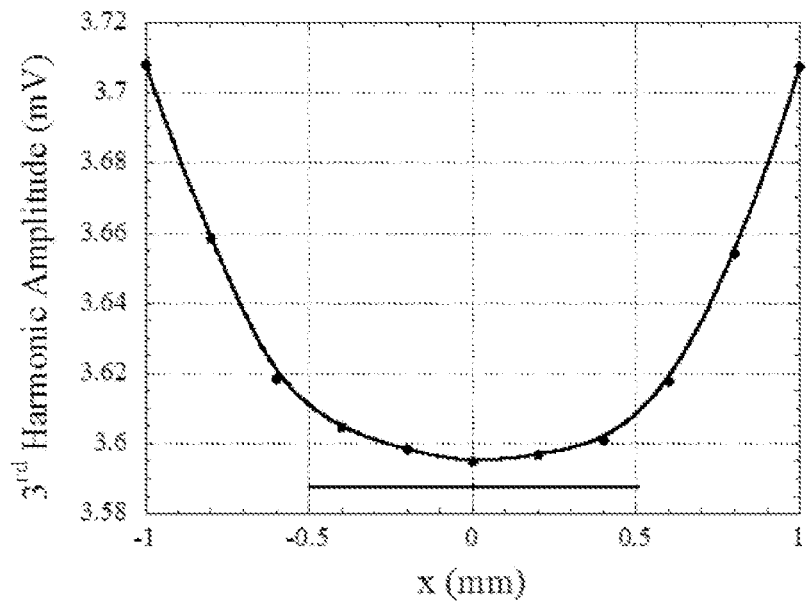
FIG. 14B is a graphical illustration of the change in the $3^{rd}$ harmonic amplitude when the sensor was moved along the x-axis of the small coil.

In addition to the applied load, the 3rd harmonic field amplitude was also found to be dependent on the position of the sensor. FIGS. 14A and 14B illustrate graphs showing the response of a high-force sensor when its position inside the small coil was varied. When moving in the z-direction and positioned within the center of each detection coil, the sensor signal was at its maximum. The sensor signal also increased when the sensor was moved away from the center of the detection coil along the x-axis or y-axis. To ensure accuracy of the measurements, it was determined that the change in the sensor signal amplitude due to position should be less than the change due the force loading. As a result, the sensor was confined into a 5 mm×5 mm×5 mm region near the center of the coil (r<2.5 mm, −2.5 mm<z<2.5 cm). The error due to position when the sensor was inside the region within the small coils was determined to be less than 0.53% of the signal amplitude, or about 4.3% of a typical full scale output of the sensor in small coil.

Figure 15A:
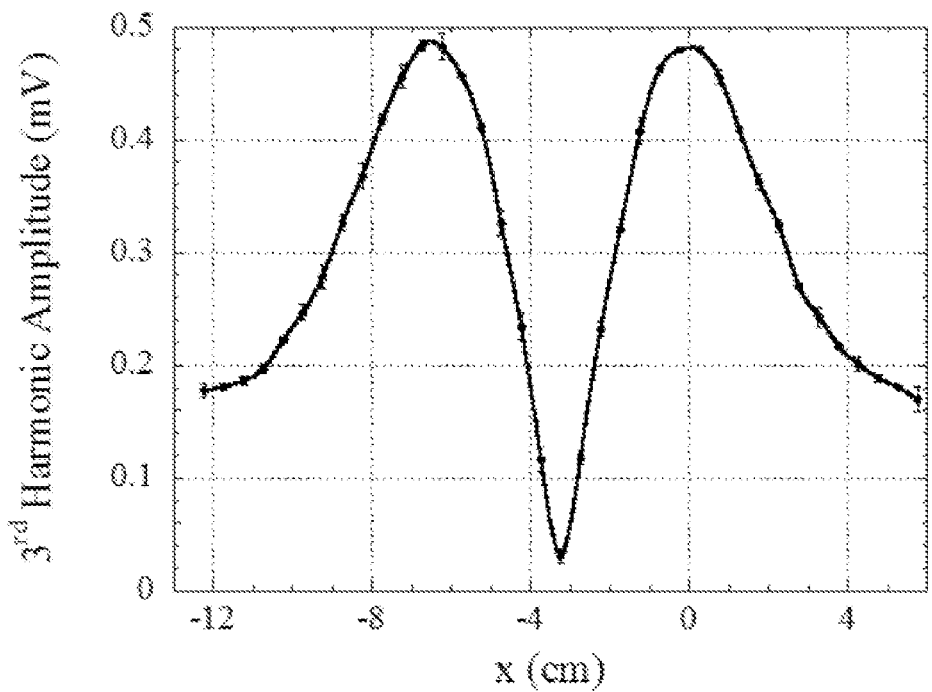
FIG. 15A is a graphical illustration of the change in the $3^{rd}$ harmonic amplitude when the sensor was moved along the z-axis of the large coil.
Figure 15B:
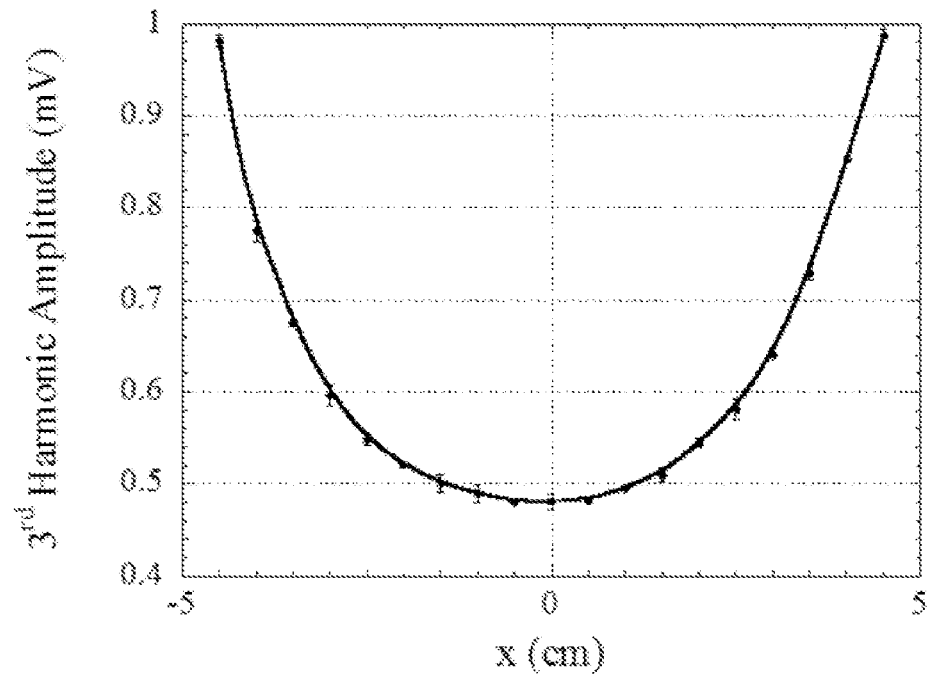
FIG. 15B is a graphical illustration of the change in the $3^{rd}$ harmonic amplitude when the sensor was moved along the x-axis of the large coil.

FIGS. 15A and 15B are graphs illustrates the response of the high-force sensor 16 when its position inside the large coil was varied. Since the coil was larger, the sensor has a larger region, thus, its position dependency was smaller than the force loading dependency. When the sensor was confined to a 10 mm×10 mm×10 mm region, the error due to position changes was 0.82% of the signal amplitude, or 2.2% of a typical full scale output of the sensor in the large coil.

Characterization of the sensor indicates the sensor has good hysteresis and low drift. Based on measurements taken during the aforementioned experiments, using a large coil can increase the relative full scale output of the sensor, but using such a coil results in a decrease in the signal amplitude. Although force measurements are sensitive to the position of the sensor, the errors are more acceptable if the sensor is within 5 mm from the center of the detection coil when using the small coil or 10 mm when using the large coil. In practice, the detection coil should be secured to the user to limit its movement.

The present invention has been described in terms of the various embodiments, and it should be appreciated that many equivalents, alternatives, variations, and modifications, aside from those expressly stated, are possible and within the scope of the invention. Therefore, the invention should not be limited to a particular described embodiment.

What is claimed is:

1. A system for monitoring a tensile force applied to a wound repairing structure, the system comprising:
    a wound repairing structure having a first end, a second end opposite the first end, and a surface, the wound repairing structure being configured to secure a wound in soft tissue;
    a magnetoelastic sensor affixed to the surface of the wound repairing structure; and
    a detection system including:
        an excitation coil configured to transmit a signal to the magnetoelastic sensor,
        a detection coil configured to produce a signal indicative of a tensile force applied to the wound repairing structure, and
        a detection unit configured to detect the signal indicative of the tensile force applied to the wound repairing structure.

2. The system of claim 1, wherein the detection system includes an electrical current generator configured to generate an electrical current in the excitation coil to thereby transmit the signal to the magnetoelastic sensor, and wherein the signal produced by the detection coil is indicative of a change in the magnetic permeability of the magnetoelastic sensor when the tensile force is applied to the wound repairing structure.

3. The system of claim 1, wherein the signal produced by the detection coil includes one of a voltage or a current in the detection coil.

4. The system of claim 1, wherein the detection system is configured to:
    excite the excitation coil with a signal having a first frequency;
    receive a signal from the detection coil having a second frequency, the second frequency is three times the value of the first frequency.

5. The system of claim 1, wherein the magnetoelastic sensor is structured so as to be located in an in vivo environment.

6. The system of claim 1, wherein the signal indicative of a tensile force includes a signal indicative of a tensile force between about 0.1N and 1.5N applied to the wound repairing structure.

7. The system of claim 1, wherein the signal indicative of the tensile force is a signal indicative of a tensile force between about 1.5N and 44.5N applied to the wound repairing structure.

8. The system of claim 1, wherein the wound repairing structure includes a first suture thread, a second suture thread; and
   wherein one end of the magnetoelastic sensor is connected to the first suture, and the opposite end of the magnetoelastic sensor is connected to the second suture.

9. The system of claim 1, wherein the wound repairing structure includes a substrate, and wherein the magnetoelastic sensor adhered to the substrate.

10. The system of claim 1, wherein the wound repairing structure includes:
   a first suture thread;
   a second suture thread; and
   a substrate having a first end attached to the first suture, and a second end attached to the second suture, the magnetoelastic sensor being connected to the substrate.

11. The system of claim 1, wherein the wound repairing structure includes (i) a first suture including a first loop, (ii) a second suture including a second loop, and (iii) a substrate including a first hook coupled to the first loop of the first suture, and a second hook coupled to the second loop of the second suture.

12. The system of claim 1, wherein the detection unit includes a current or voltage detector that detects a current or voltage induced in the detection coil.

13. The system of claim 1, wherein the excitation coil is configured to generate an alternating current magnetic field so as to generate the signal transmitted to the magnetoelastic sensor.

14. The system of claim 1, wherein the excitation coil is arranged concentric with the detection coil, and a diameter of the excitation coil is larger than a larger diameter of the detection coil.

15. The system of claim 1, wherein the wound repairing structure includes a bone anchor and a suture coupled to the bone anchor.

16. The system of claim 1, wherein the magnetoelastic sensor includes a biodegradable material.

17. The system of claim 1, wherein the wound repairing structure includes a suture thread, and wherein the magnetoelastic sensor is a magnetoelastic coating disposed on a surface of the suture thread.

18. The system of claim 1, further comprising an enclosure surrounding the magnetoelastic sensor configured to protect the sensor from a surrounding environment.

19. The system of claim 1, wherein the wound repairing structure includes (i) a bone anchor, and (ii) a fixation rod and (iii) a suture, wherein the fixation rod and the suture are coupled to the bone anchor, and the magnetoelastic sensor is attached to the bone anchor.

20. The system of claim 1, wherein the wound repairing structure includes (i) a bone anchor, (ii) a fixation rod coupled to the bone anchor, and (iii) and a suture coupled to the fixation rod, wherein the magnetoelastic sensor is attached to one of the fixation rod or the suture.

21. A method for monitoring a force applied to a wound repairing structure having a first end, a second end opposite the first end, and a surface defined between the first end and the second end, the method comprising:
   providing the wound repairing structure having a magnetoelastic sensor affixed to the surface of the wound repairing structure;
   securing one end of the wound repairing structure to soft tissue;
   transmitting a signal from an excitation coil to the magnetoelastic sensor coupled to a wound repairing structure;
   producing, at a detection coil, a signal a indicative of a tensile force applied to the wound repairing structure; and
   detecting the signal indicative of the tensile force applied to the wound repairing structure.

22. The method of claim 21, wherein the transmitted signal includes a magnetic field.

23. The method of claim 21, which includes generating an alternating current in the excitation coil so as to produce the signal transmitted from the excitation coil to the magnetoelastic sensor.

* * * * *